United States Patent [19]

Schaar

[11] 4,182,333
[45] Jan. 8, 1980

[54] DISPOSABLE DIAPER WITH FASTENER RETAINED END BARRIER

[75] Inventor: Charles H. Schaar, Lake Zurich, Ill.

[73] Assignee: Colgate-Palmolive Company, New York, N.Y.

[21] Appl. No.: 823,259

[22] Filed: Aug. 10, 1977

[51] Int. Cl.² ............................................. A61F 13/16
[52] U.S. Cl. ............................ 128/287; 128/DIG. 30
[58] Field of Search .................. 128/284, 287, 290 R, 128/290 P

[56] References Cited

U.S. PATENT DOCUMENTS

| | | | |
|---|---|---|---|
| 3,893,460 | 7/1975 | Karami | 128/287 |
| 3,921,638 | 11/1975 | Schaar | 128/287 |
| 3,951,150 | 4/1976 | Schaar | 128/287 |

*Primary Examiner*—Robert W. Michell
*Assistant Examiner*—C. W. Shedd
*Attorney, Agent, or Firm*—Powell L. Sprunger

[57] ABSTRACT

A disposable diaper comprising, an absorbent pad assembly having an absorbent pad, a front surface, a back surface, a pair of side edges, and a pair of end edges connecting the side edges. The pad assembly has a plurality of longitudinally extending folds defining a box-pleat configuration of the pad assembly having a pair of first fold lines defining a longitudinally extending central panel, and a pair of second fold lines defining a pair of first pleat panels intermediate the first and second fold lines and overlying the central panel, and defining a pair of second pleat panels extending from the second fold lines. The pad assembly has a lateral fold of the box-pleat assembly along a fold line spaced slightly from one of the end edges and defining an end section of the pad assembly intermediate the lateral fold line and the one end edge, with the end section being folded over the front surface of an adjacent portion of the pad assembly. The diaper has a tape fastener comprising, a release sheet on the back surface of the end section, and a tape strip having a first inner section attached to a second pleat panel beneath the central panel of the folded over end section. The tape strip also has a second outer section extending around the back surface of the end section and having an adhesive surface releasably attached to the release sheet.

10 Claims, 10 Drawing Figures

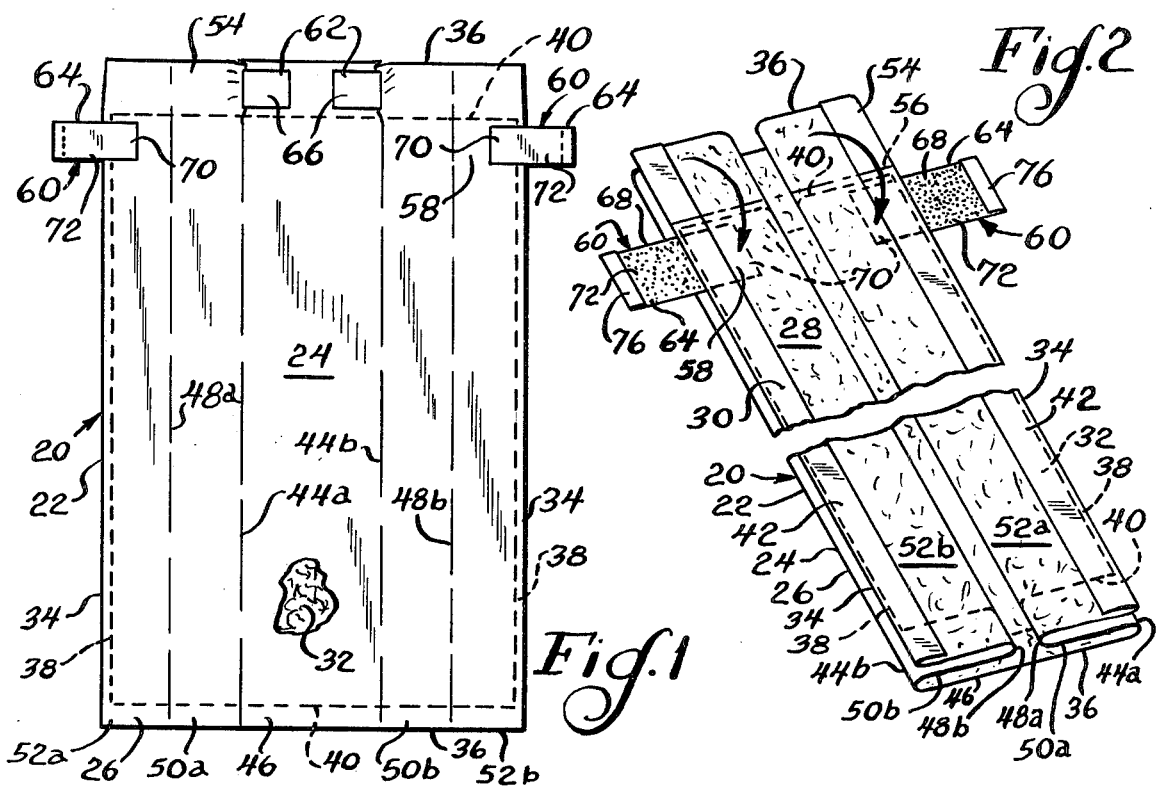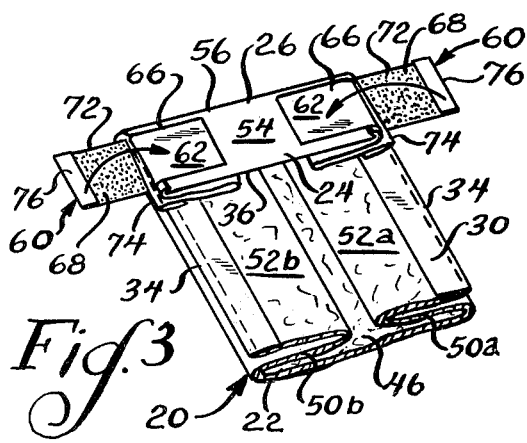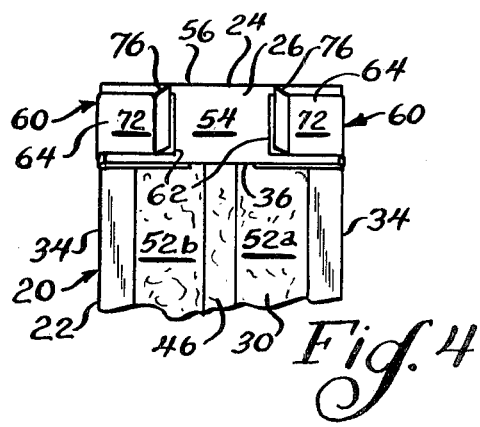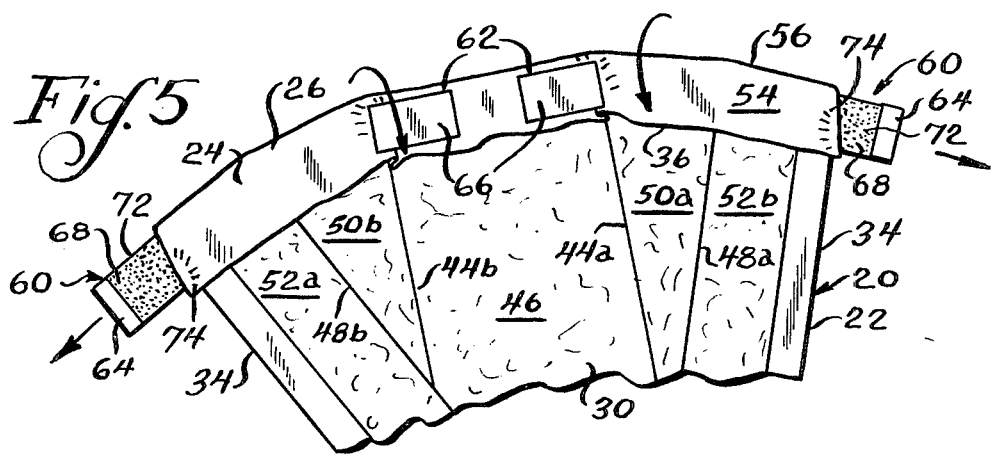

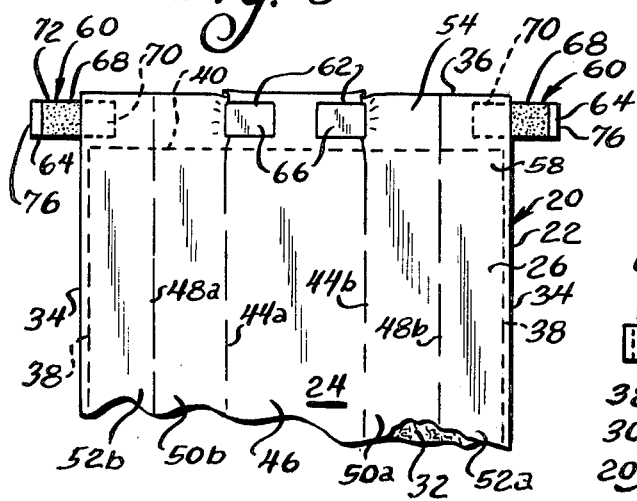
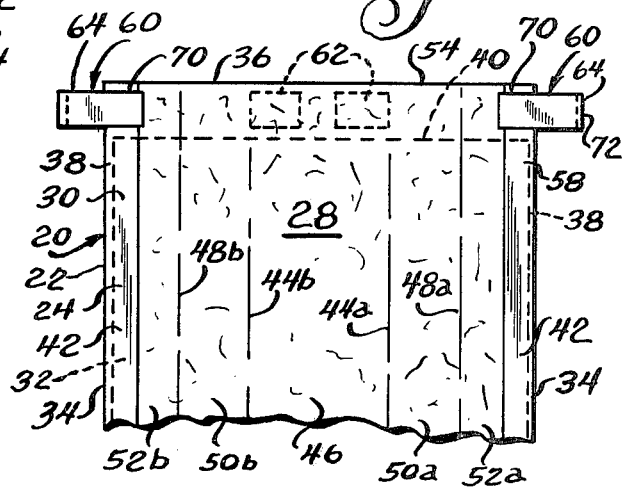
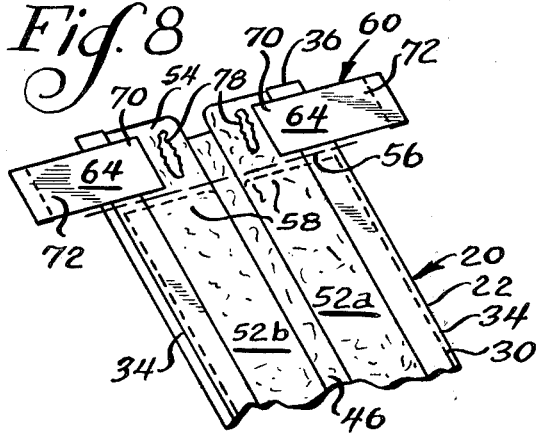
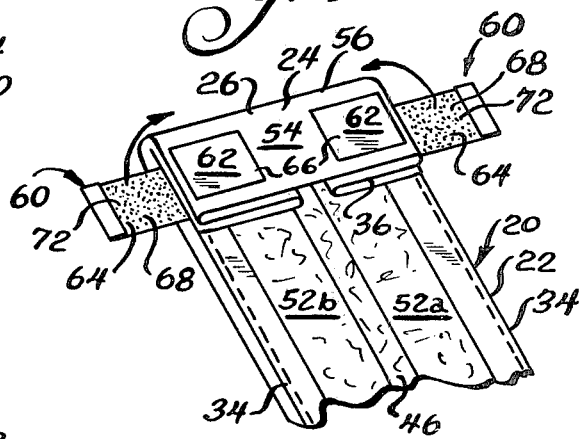
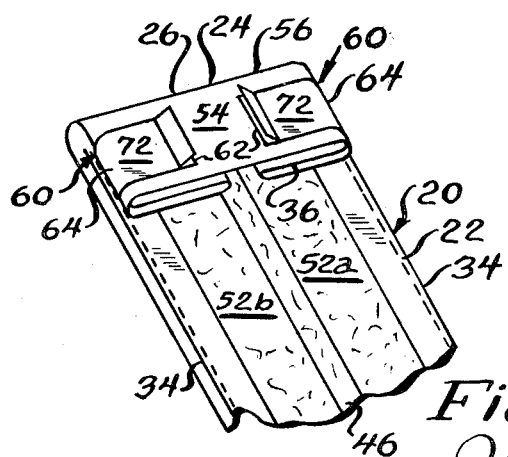

DISPOSABLE DIAPER WITH FASTENER RETAINED END BARRIER

BACKGROUND OF THE INVENTION

The present invention relates to absorbent articles, and more particularly to disposable diapers.

A various assortment of disposable diapers have been proposed for use on infants, and have become increasingly popular with parents since they may be discarded after a single use and need not be laundered. Such diapers are normally constructed having a fluid impervious backing sheet, a fluid pervious top or cover sheet, and an absorbent pad intermediate the backing and cover sheets. The diapers have also been provided with tape fasteners normally having a securement portion having adhesive covered with a release sheet.

One of the problems associated with such diapers has been recurrent leakage from the absorbent pad in the waistline portion. Further, it is desirable that the release sheets of such fasteners are not separated from the diaper when removed from the securement portions, since such loose release sheets must be discarded by the parents during placement of the diaper, thus causing inconvenience of necessary disposal.

SUMMARY OF THE INVENTION

A principal feature of the present invention is the provision of a disposable diaper which minimizes leakage from an end of the diaper during use.

The diaper of the present invention comprises, an absorbent pad assembly having an absorbent pad, a front surface, a back surface, a pair of side edges, and a pair of end edges connecting the side edges. The pad assembly has a plurality of longitudinally extending folds defining a box-pleat configuration of the pad assembly having a pair of first fold lines defining a longitudinally extending central panel, and a pair of second fold lines defining a pair of first pleat panels intermediate the first and second fold lines and overlying the central panel, and defining a pair of second pleat panels extending from the second fold lines. The pad assembly has a lateral fold of the box-pleat assembly along a fold line spaced slightly from one of the end edges and defining an end section of the pad assembly intermediate the lateral fold line and the one end edge, with the end section being folded over the front surface of an adjacent portion of the pad assembly. The diaper has a tape fastener comprising, release sheet means on the back surface of the end section, and a tape strip having a first inner section attached to a second pleat panel beneath the central panel of the folded over end section. The tape strip has a second outer section extending around the back surface of the end section and having an adhesive surface releasably attached to the release sheet means.

A feature of the present invention is that the fastener retains the end section in its overlying configuration of the pad assembly prior to lateral unfolding of the diaper.

Thus, a feature of the present invention is that the fastener retains an end portion of the diaper in a folded configuration to facilitate passage of the end through the infant's legs during placement.

Yet another feature of the invention is the provision of means for retaining the end section against the adjacent portion of the pad assembly during lateral unfolding of the diaper.

Thus, a feature of the present invention is that a fluid impervious backing sheet in the retained end section provides a barrier to prevent fluid leakage from the end of the absorbent pad.

Still another feature of the invention is that the tape fastener eliminates the necessity for discarding separate release sheets during placement of the diaper.

Further features will become more fully apparent in the following description of the embodiments of this invention and from the appended claims.

DESCRIPTION OF THE DRAWINGS

In the drawings:

FIG. 1 is a front plan view, partly broken away, of a disposable diaper of the present invention;

FIG. 2 is a fragmentary front perspective view of the diaper of FIG. 1 as folded into a box-pleat configuration;

FIG. 3 is a fragmentary perspective view illustrating an end section of the diaper of FIG. 2 as folded over a front of the diaper;

FIG. 4 is a fragmentary plan view of the diaper of FIG. 3 illustrating tape fasteners as retaining the end section in place;

FIG. 5 is a fragmentary front plan view of the diaper of FIG. 4 as unfolded during placement on an infant;

FIG. 6 is a fragmentary back plan view of another embodiment of a disposable diaper of the present invention;

FIG. 7 is a fragmentary front plan view of the diaper of FIG. 6;

FIG. 8 is a fragmentary front perspective view of the diaper of FIGS. 6 and 7 as folded into a box-pleat configuration;

FIG. 9 is a fragmentary perspective view illustrating an end section of the diaper of FIG. 8 as folded over the front of the diaper; and FIG. 10 is a fragmentary perspective view illustrating tape fasteners of the diaper as retaining the end section in place.

DESCRIPTION OF THE PREFERRED EMBODIMENTS

Referring now to FIGS. 1 and 2, there is shown a disposable diaper generally designated 20 having an absorbent pad assembly 22. The pad assembly 22 has a fluid impervious backing sheet 24, such as polyethylene, defining a back surface 26 of the pad assembly 22, a fluid pervious cover or top sheet 28, such as a nonwoven material, defining a substantial portion of a front surface 30 of the pad assembly 22, and an absorbent pad 32 located intermediate the backing sheet 24 and top sheet 28. As shown, the pad assembly has a pair of side edges 34, and end edges 36 connecting the side edges 34. The absorbent pad 32 also has a pair of side edges 38 and end edges 40 connecting the side edges 38. In a preferred embodiment, as shown, the end edges 40 of the absorbent pad 32 are spaced from the end edges 36 of the pad assembly 22, and the side edges 38 of the absorbent pad 32 are located adjacent the side edges 34 of the pad assembly 22. The backing sheet 24 has lateral side margins 42 folded over and secured to the top sheet 28, such that the side margins 42 of the backing sheet 24 cover lateral side margins of the absorbent pad 32.

As shown, the pad assembly 22 is longitudinally folded along a plurality of fold lines from the flat configuration of FIG. 1 to a box-pleat configuration of FIG. 2. Thus, the pad assembly 22 is folded along a first pair of longitudinally extending fold lines 44a and 44b to define a central panel 46 intermediate the first fold lines 44a and b. Additionally, the pad assembly is folded along a second pair of longitudinally extending fold lines 48a and 48b in order to define a first pair of pleat panels 50a and 50b intermediate the first and second fold lines, with the first pleat panels extending from the central panel 46 and overlying the central panel. Additionally, the second fold lines 48a and b define a second pair of pleat panels 52a and 52b intermediate the second fold lines and the associated side edge of the pad assembly, with the second pleat panels overlying the respective first pleat panels.

With reference to FIG. 2, the pad assembly 22 has an end section 54 in a waistline portion of the diaper. The end section 54 includes an end portion of the backing sheet 24 which is folded along a lateral fold line 56 with the end section 54 overlying the front of the diaper. Thus, the front surface 30 of the end section 54 faces the front surface of an underlying adjacent portion 58 of the pad assembly adjacent the fold line 56, such that the back surface 26 of the end section 54 faces outwardly from the front of the diaper. In a preferred form, as shown, the fold line 56 is located adjacent the end edge 40 of the absorbent pad 32, and is located intermediate the end edge 40 of the absorbent pad 32 and the end edge 36 of the pad assembly 22. In the folded over configuration, the end section 54 thus overlies an end margin of the absorbent pad 32, and the fluid impervious backing sheet in the end section 54 provides a fluid impervious barrier at the end of the absorbent pad to prevent leakage from the absorbent pad of the pad assembly when it is laterally unfolded during use of the diaper, as will be seen below.

With reference to FIGS. 1 and 2, the diaper 20 also has a pair of tape fasteners generally designated 60. Each of the tape fasteners 60 has a release sheet 62 and a pressure-sensitive tape strip 64. As shown in FIG. 1, the release sheets 62 are secured to the back surface 26 of the central panel 46 in the end section 54, with the release sheets being located adjacent the first longitudinal fold lines 44a and b. The release sheets 62 have an outer release surface 66, and, as shown, may extend substantially the width of the end section 54.

With reference to FIGS. 1 and 2, each of the tape strips 64 has adhesive 68 on a surface thereof. The tape strips 64 have a first inner end section 70 attached to the back surface 26 of the pad assembly 22 on the second pleat panels 52a and b in the adjacent portion 58 of the pad assembly. In addition, the tape strips 64 have second outer end sections 72 extending past the associated side edges 34 of the pad assembly.

With reference to FIG. 2, the end section 54 of the pad assembly 22 is folded over the front surface of the adjacent portion 58 of the pad assembly while the second sections 72 of the tape strips 64 extend outwardly from the pad assembly. In a preferred form, as shown in FIG. 3, side portions 74 of the second pleat panels 52a and b in the end section 54 are attached to adhesive 68 on the second strip sections 72 adjacent the side edges 34 of the pad assembly for a purpose which will be described below. Next, with reference to FIG. 3, the second end sections 72 of the tape strips 64 are folded over the back surface 26 of the end section 54, and the adhesive on the second strip sections 72 is releasably attached to the release surface 66 of the associated release sheets 72 resulting in the folded diaper illustrated in FIG. 4. If desired, the second strip sections 72 may have folded over end portions 76 which serve as tabs to facilitate removal of the second strip sections 72 from the release sheets 62 during placement of the diaper.

It will be apparent that the fasteners 60 of the present invention retain the diaper end section in a folded configuration and thus prevent premature unfolding of the diaper end. When it is desired to secure the diaper about an infant, the second strip sections 72 of the fasteners 60 are peeled from the associated release sheet 62 in order to free the central portion of the end section 54. Next, with reference to FIG. 5, the waistline portion of the diaper is laterally unfolded, and the second strip sections 72 may be attached to the other waistline portion of the diaper in order to secure the diaper about the infant. In addition, it will be seen that the side portions 74 of the end section 54 remain affixed to the tape strips 64, and retain the end section 54 in its folded over configuration after the diaper end portion has been laterally unfolded. Thus, the fluid impervious backing sheet of the end section 54 overlies an end portion of the absorbent pad in order to minimize the possibility of leakage from the end of the pad during use of the diaper.

Another embodiment of the present invention is illustrated in FIGS. 6-10, in which like reference numerals designate like parts. As before, the pad assembly 22 has a plurality of longitudinally extending fold lines defining a central panel 46, a first pair of pleat panels 50a and b extending from the central panel 46, and a second pair of pleat panels 52a and b extending from the first pleat panels 50a and b. This diaper embodiment also has an end section 54 defined by a lateral fold line 56, and has a pair of release sheets 62 secured to the back surface 26 of the end section 54 adjacent the first fold lines 44a and b. The fasteners 60 of this embodiment also have a pair of tape strips 64 with first end sections 70 being secured to the associated second pleat panels 52a and b. However, in this embodiment, the first strip sections 70 are secured to the front surface 30 of the end section 54 adjacent the side edges 34 of the pad assembly 22. Thus, the pad assembly 22 is folded into a box-pleat configuration with the second sections 72 of the tape strips 64 extending outwardly from the pad assembly 22, as shown in FIG. 8. The end section 54 is then folded about the lateral fold line 56 over the front surface of the adjacent portion 58 of the pad assembly 22 in order to form the pad assembly into the configuration illustrated in FIG. 9. However, in a preferred form as shown in FIG. 8, the pad assembly 22 preferably has adhesive lines or spots 78 which are located intermediate the end section 54 and the adjacent portion 58 of the pad assembly on the second pleat panels 52a and b. In this manner, the second pleat panels 52a and b of the end section 54 are bonded to the second pleat panels 52a and b of the adjacent portion 58 of the pad assembly for a purpose which will be described below.

Referring again to FIG. 9, the second sections 72 of the tape strips 64 are folded over the back surface 26 of the central panel 46 in the end section 54, and the adhesive 68 of the second strip sections 72 is releasably attached to the release surfaces 66 of the release sheets 62. In this manner, the end section 54 is retained in its folded over configuration, as illustrated in FIG. 10, thus preventing premature unfolding of the associated waistline portion of the diaper.

In use, the second sections 72 of the tape strips 64 may be peeled from the associated release sheet 62, and the pad assembly may be laterally expanded as previously discussed in connection with the diaper of FIGS.

1-5. In this configuration, the second strip sections 72 extend past the side edges of the pad assembly for use in securing the diaper about the infant. In addition, the adhesive lines 78 previously discussed in connection with FIG. 8 retain the second pleat panels 52a and b of the end section 54 and adjacent portion 58 together in order to retain the end section 54 in its folded over configuration after lateral expansion of the diaper. In this manner, the end section 54 serves as a fluid impervious barrier over an end portion of the pad to minimize the possibility of leakage of body fluids from the end of the pad.

The foregoing detailed description is given for clearness of understanding only, and no unnecessary limitations should be understood therefrom, as modifications will be obvious to those skilled in the art.

I claim:

1. A disposable diaper, comprising:
   an absorbent pad assembly having an absorbent pad, a front surface, a back surface, a pair of side edges, a pair of end edges connecting the side edges, a plurality of longitudinally extending folds defining a box-pleat configuration of the pad assembly having a pair of first fold lines defining a longitudinally extending central panel, and a pair of second fold lines defining a pair of first pleat panels intermediate the first and second fold lines and overlying the central panel, and defining a pair of second pleat panels extending between the second fold lines and said side edges, said pad assembly having a lateral fold of the box-pleat assembly along a fold line spaced slightly from one of said end edges and defining an end section of the pad assembly intermediate said lateral fold line and said one end edge, with said end section being folded over the front surface of a portion of the pad assembly adjacent said lateral fold line; and
   a tape fastener comprising release sheet means on the back surface of said end section central panel at a location adjacent a first fold line of the central panel and having a release surface facing outwardly from the back surface of said end section central panel, and a tape strip having a first inner section attached to a second pleat panel beneath the central panel of the folded over end section, and a second outer section extending around the side edge and over a portion of the back surface of said end section central panel and having an adhesive surface facing the back surface of said end section central panel and releasably attached to said release sheet means with said release surface facing outwardly from the back surface of the end section central panel.

2. The diaper of claim 1 wherein said first section of the tape strip is attached to said adjacent portion of the pad assembly.

3. The diaper of claim 2 wherein said first section of the tape strip is attached to the back surface of said second panel.

4. The diaper of claim 2 wherein a side portion of said end section adjacent a side edge of the end section is attached to said tape strip adjacent a side edge of said adjacent pad assembly portion.

5. The diaper of claim 1 wherein said first section of the tape strip is secured to said end section.

6. The diaper of claim 5 wherein said first section of the tape strip is secured to the front surface of said second panel.

7. The diaper of claim 1 wherein the length of said end section is slightly larger than the width of said release sheet means.

8. The diaper of claim 1 including means for retaining said end section against said adjacent portion of the pad assembly when said diaper is laterally unfolded.

9. The diaper of claim 1 wherein said pad assembly includes a backing sheet of fluid impervious material defining said back surface and extending to said one end edge of the pad assembly, in which said pad has an end edge spaced from said one end edge of the pad assembly, and in which said lateral fold line is located adjacent the pad end edge intermediate the pad end edge and said pad assembly one end edge.

10. The diaper of claim 1 wherein said end section overlies an end portion of the pad and is spaced from said pad.

* * * * *